(12) United States Patent
Hill (10) Patent No.: US 8,291,607 B2
(45) Date of Patent: Oct. 23, 2012

(54) GONIOMETRIC POSITIONING SYSTEM

(76) Inventor: Philip A. Hill, Urbana, OH (US)

( * ) Notice: Subject to any disclaimer, the term of this patent is extended or adjusted under 35 U.S.C. 154(b) by 443 days.

(21) Appl. No.: 12/708,567

(22) Filed: Feb. 19, 2010

(65) Prior Publication Data

US 2010/0212449 A1 Aug. 26, 2010

Related U.S. Application Data

(60) Provisional application No. 61/154,354, filed on Feb. 20, 2009.

(51) Int. Cl.
*G01B 5/25* (2006.01)
*B23Q 16/00* (2006.01)

(52) U.S. Cl. ............... 33/568; 33/573; 33/286

(58) Field of Classification Search ............ 33/286, 33/1 CC, 1 MP, 549, 567, 567.1, 568, 569, 33/573
See application file for complete search history.

(56) References Cited

U.S. PATENT DOCUMENTS

| | | | | |
|---|---|---|---|---|
| 2,676,414 A * | 4/1954 | Derry | | 33/534 |
| 3,288,421 A * | 11/1966 | Peterson | | 248/396 |
| 4,575,942 A * | 3/1986 | Moriyama | | 33/1 M |
| 4,607,578 A * | 8/1986 | Inoue et al. | | 108/145 |
| 5,207,097 A * | 5/1993 | Gutman | | 73/162 |
| 6,705,019 B2 * | 3/2004 | Mauro | | 33/569 |
| 7,275,332 B2 * | 10/2007 | Blanding | | 33/568 |
| 7,523,582 B1 * | 4/2009 | Ahrens et al. | | 42/115 |
| 7,735,390 B2 * | 6/2010 | Nabat et al. | | 74/490.03 |
| 8,074,369 B2 * | 12/2011 | McMurtry | | 33/503 |
| 8,091,243 B2 * | 1/2012 | Bos | | 33/1 M |
| 2002/0083603 A1 * | 7/2002 | Jang | | 33/281 |
| 2009/0260243 A1 * | 10/2009 | Evans et al. | | 33/502 |

OTHER PUBLICATIONS

"NLX to Deliver Beechjet Simulator," Flight Magazine, Aug. 2001. http://www.flightglobal.com/news/articles/nlx-to-deliver-beechjet-simulator-135260/, visited Feb. 22, 2012.
Photographs and description of a positioner device.

* cited by examiner

*Primary Examiner* — Christopher Fulton
(74) *Attorney, Agent, or Firm* — Michael A. Forhan; James R. Eley; Eley Law Firm Co., LPA (57) ABSTRACT

A system for positioning an object includes a base and a platform for detachably retaining the object. A first linear actuator is pivotably coupled to a first pivot axis of the platform and a first pivot axis of the base. A second and a third linear actuator are pivotably coupled to a second pivot axis of the base and the first pivot axis of the platform. A fourth linear actuator is pivotably coupled to the second pivot axis of the base and a second pivot axis of the platform. The first, second, third and fourth linear actuators being selectably adjustable in length to position the platform at a select position about a predetermined arc of travel.

20 Claims, 8 Drawing Sheets

GONIOMETRIC POSITIONING SYSTEM

This application claims priority to U.S. provisional application 61/154,354, filed Feb. 20, 2009, the contents of which are hereby incorporated by reference.

FIELD

The present invention relates generally to photometric test and measurement equipment, and in particular to a goniometric positioning system for use in conjunction with photometric test and measurement equipment.

BACKGROUND

Goniometric multi-axis positioners (generally called "goniometers" and "goniophotometers") have been available for a number of years in the lighting industry. Goniometers are used to accurately and precisely position and orient a test object at a plurality of positions in order to evaluate the object's photometric properties, for example the spatial luminous intensity distribution of a light emitting or light reflecting object. Goniometers are typically described as having either a "Type A" or "Type B" configuration. An example Type A goniometer 10 is shown in FIG. 1, while a Type B goniometer 100 is shown in FIG. 2.

Figure 1:
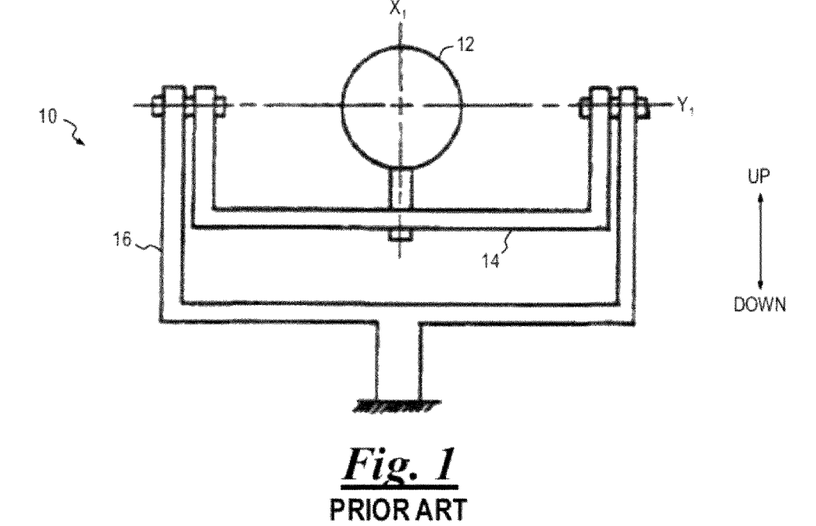
FIG. 1 is a prior art Type A goniometer.

With reference to FIG. 1, Type A goniometer 10 is a common configuration used in the transportation lighting industry. Goniometer 10 includes a test platform 12 attached to an inner frame member 14 and is rotatable with respect to the inner frame member about an axis of rotation "$X_1$." Inner frame member 14 is attached to an outer frame member 16 and is rotatable with respect to the outer frame member about an axis of rotation "$Y_1$." Thus, the "left-right" rotational axis $X_1$ is nested within the tilt or "up-down" axis $Y_1$. This basic configuration is widely used to test automobile, aircraft and other transportation lighting devices.

Figure 2:
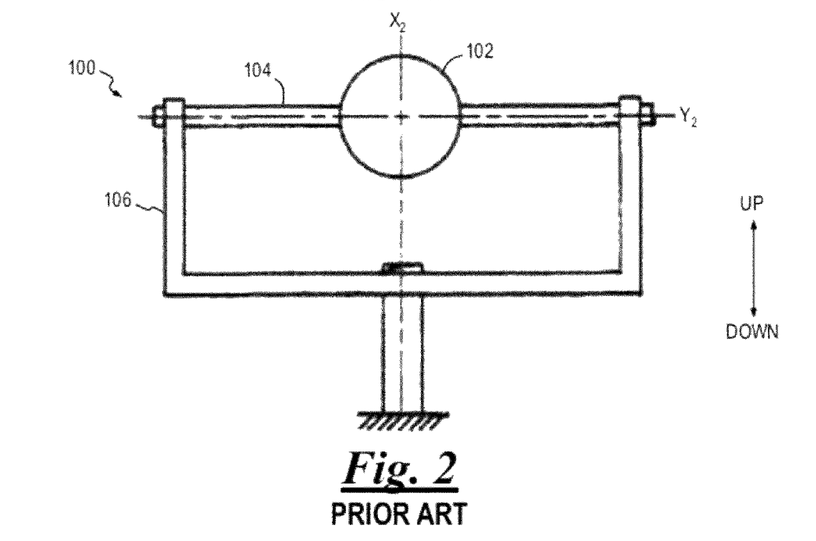
FIG. 2 is a prior art Type B goniometer.

With reference to FIG. 2, Type B goniometer 100 includes a platform 102 attached to a horizontal member 104. Horizontal member 104 is rotatably attached to a frame member 106. Platform 102, horizontal member 104 and frame member 106 are all rotatable together about an axis of rotation "$X_2$." Platform 102 and horizontal member 104 are also further rotatable together about a tilt axis "$Y_2$." As can be seen from FIG. 2, Type B goniometer 100 is configured such that rotational axis $X_2$ is located beneath tilt axis $Y_2$. Accordingly, the entire frame 106 of the goniometer rotates for the right-left motion. This type of goniometer is commonly used for testing of displays and commercial lighting fixtures.

Some variations of the basic goniometer design exist. For example, some goniometer systems have been built in a "half frame" configuration 200, shown generally in FIG. 3. In the half-frame configuration a platform 202 is fixed to an inner frame 204, the inner frame being cantilevered from an outer frame 206. Platform 202 is rotatable about a rotational axis $X_3$. In addition, inner frame 204 and platform 202 are rotatable together about a tilt axis $Y_3$. A test object (not shown for clarity) may also be adjusted to a desired height $H_3$ by fixturing or tooling equipment that is either incorporated into platform 202 or is detachably coupled to the platform.

Figure 3:
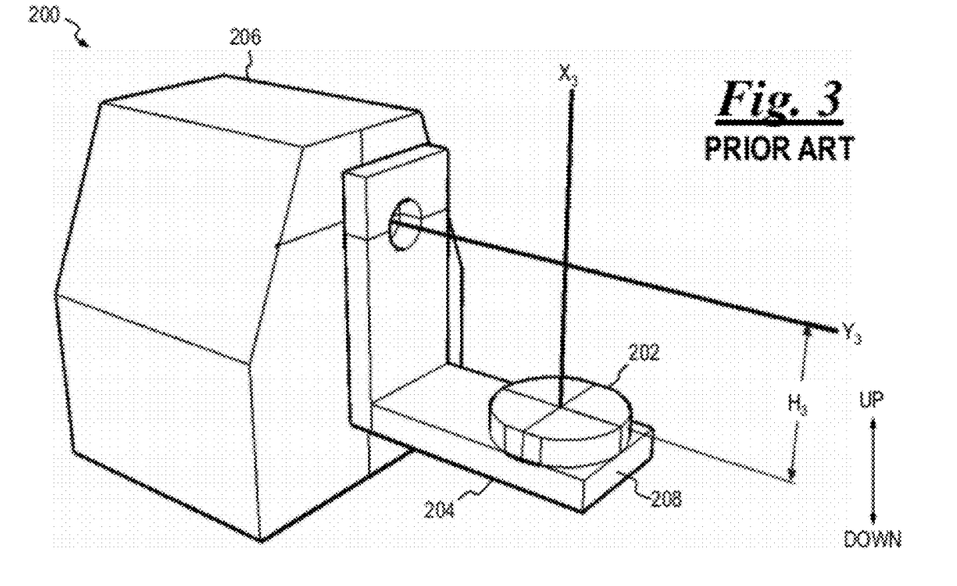
FIG. 3 is a prior art half-frame Type A goniometer.

The open-end cantilever goniometer 200 of FIG. 3 has some advantages over the closed-box frame designs of FIGS. 1 and 2 due to the lack of an outer frame 206 member at an unsupported end 208 of inner frame 204. As can be appreciated by comparing FIG. 3 with FIGS. 1 and 2, an outer frame 206 member proximate end 208 could interfere with the movement of inner frame 204 in situations where a large test object is attached to platform 202. However, given that many vehicle lighting devices have a left-hand and a right-hand configuration, there is still the potential for interference in some testing scenarios. For example, while no test object-to-outer frame 206 interference may be experienced at the unsupported end 208 of inner frame 204, interference between the test object and the outer frame may still occur on the opposing, supported side of the inner frame. The nature of the half-frame goniometer design also requires a relatively large, heavy structure and massive bearing assemblies to minimize positional error with regard to platform 202 due to deflection of the cantilevered inner frame 204. In some cases this drawback lends an advantage to the box closed-frame designs of goniometers 10, 100 due to their inherently balanced weight distribution.

Figure 4:
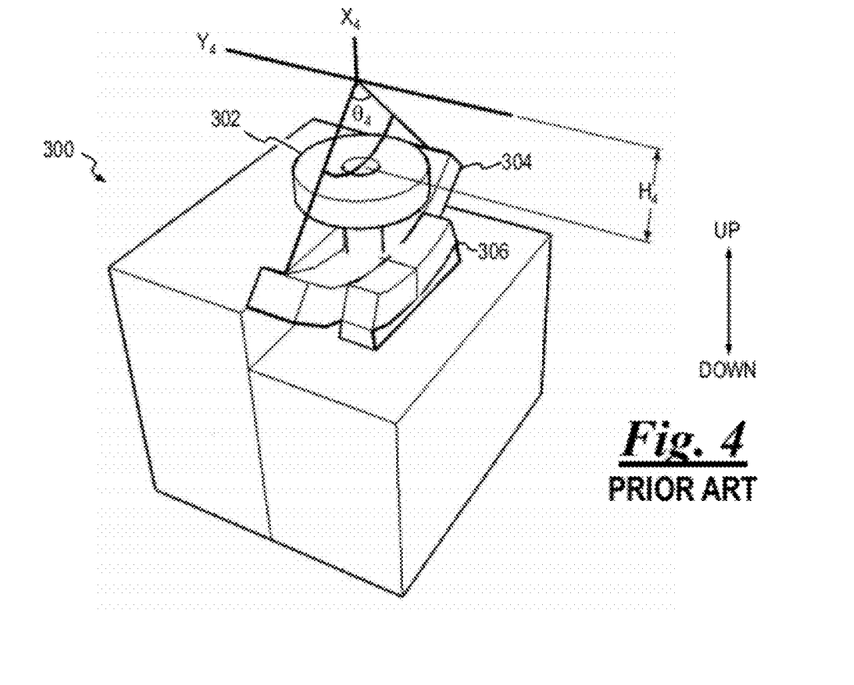
FIG. 4 is a prior art sector gear goniometer.
Figure 5:
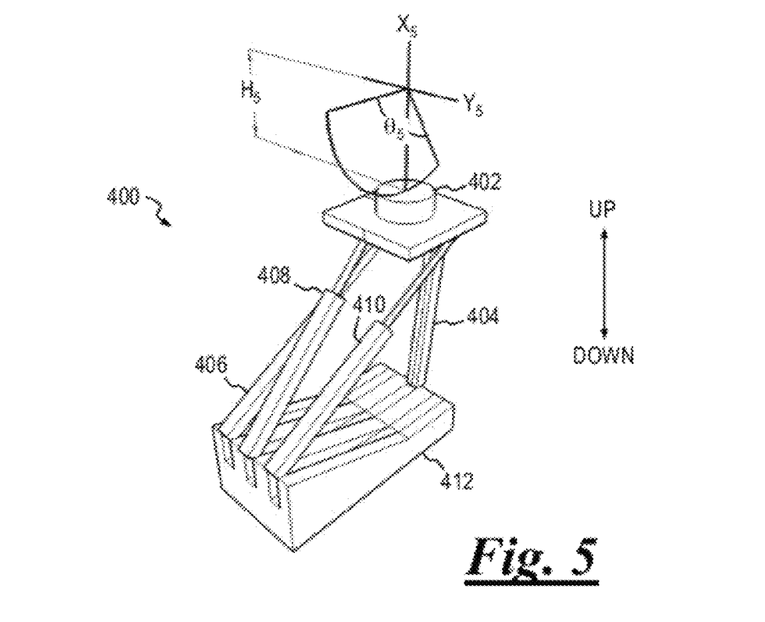
FIG. 5 is a rear-quarter view of a goniometer positioning system according to an embodiment of the present invention.
Figure 6:
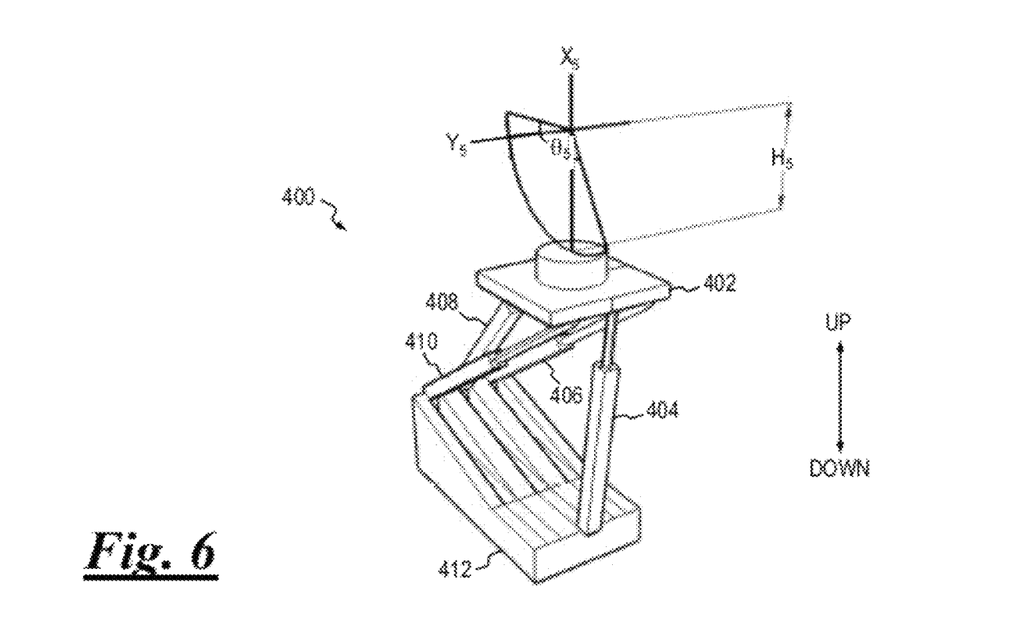
FIG. 6 is a front view of the goniometer system of FIG. 5.

A third configuration of goniometer, known as a "sector gear positioner" 300, is shown in FIG. 4. This positioner is a reapplication of a type of positioner used for antennae and artillery aiming devices. A platform 302 is affixed to a large sector gear 304 and is rotatable about a rotational axis $X_4$. The sector gear 304 is coupled to a gear drive 306 that moves the sector gear and platform together to predetermined positions about a tilt axis $Y_4$ having a range of motion $\theta_4$. A test object (not shown for clarity) may also be adjusted to a desired height $H_4$ by fixturing or tooling equipment that is either incorporated into platform 302 or is detachably coupled to the platform.

A disadvantage of sector gear positioner 300 is that the range $\theta_4$ of up-down motion of platform 302 is limited to a tilt angle of about ±30 degrees from a horizontal orientation due to the sector gear 304 interfering with a light emission path of a test object mounted to the platform at tilt angle extremes. For most transportation lighting it is necessary to run some tests with the light emission of the test object oriented to about a 90-degree "up" position. This is particularly true with respect to forward lighting, such as headlamps for automobiles, as well as aerospace lighting. The "down" direction, i.e., the light emission of the test object oriented to about 180-degrees from the "up" position, is not as much of an issue because all goniometers are limited in this direction due to the mounting requirements of most test objects.

As can be appreciated from the foregoing discussion, current goniometers suffer from significant limitations with regard to the size and shape of objects that can be tested, due to the potential for interference between the test object and the structure of the goniometer. This interference limits the range of motion of the goniometer, in turn limiting the amount of photometric data that can be gathered. Current goniometers also typically consume a significant amount of laboratory space that could otherwise be used for other purposes. Furthermore, available goniometers are typically extremely heavy, making them expensive to transport and requiring significant foundational support at their point of installation. There is a need for a goniometer that addresses these shortcomings.

SUMMARY

A goniometric positioning system is disclosed according to an embodiment of the present invention. The system employs a set of linear actuators configured as a four-bar linkage to achieve the desired goniometer test article positioning characteristics.

One aspect of the invention is a system for positioning an object for photometric testing. The system includes a base, and a platform for detachably retaining the object. A first linear actuator is pivotably coupled to a first pivot axis of the platform and a first pivot axis of the base. A second and a third linear actuator are pivotably coupled to a second pivot axis of the base and the first pivot axis of the platform. A fourth linear actuator is pivotably coupled to the second pivot axis of the base and a second pivot axis of the platform. The first, second, third and fourth linear actuators are selectably adjustable in length to position the platform at a select position about a predetermined arc of travel.

BRIEF DESCRIPTION OF THE DRAWINGS

Further features of the inventive embodiments will become apparent to those skilled in the art to which the embodiments relate from reading the specification and claims with reference to the accompanying drawings, in which:

DETAILED DESCRIPTION

A goniometric positioning system 400 is shown in FIGS. 5 through 10 according to an embodiment of the present invention. Goniometer 400 comprises a platform 402 that is movably supported by adjustable-length members such as a set of linear actuators 404, 406, 408 and 410, each being pivotably coupled to and extending between the platform and a fixed base 412. Linear actuator 404 is pivotably coupled between a pivot axis $PA_1$ at base 412 and a pivot axis $PA_2$ at platform 402. Linear actuators 406, 410 are pivotably coupled between a pivot axis $PA_3$ of base 412 and pivot axis $PA_2$. Linear actuator 408 is pivotably coupled between pivot axis $PA_3$ of base 412 and a pivot axis $PA_4$ of platform 402.

Linear actuators 404, 406, 408, 410 may be any type of device now known or later invented that applies force in a linear manner. Example types of linear actuators include, without limitation, rotary-to-linear motion converters such as electro-mechanical actuators, segmented spindle actuators and moving coil actuators. Other types of linear actuators may directly generate linear force, such as hydraulic actuators, piezoelectric actuators, linear motors and wax motors.

With reference to FIGS. 9A through 9D, if linear actuators 404, 406, 408, 410 are provided as electro-mechanical actuators they may each comprise an electric motor 411 such as, without limitation, a dc brush, dc brushless, stepper and induction motor. The motor is coupled to a rotary-to-linear motion converter 413. The rotary-to-linear motion converter may be, without limitation, a lead screw or ball screw. The electric motor may be directly coupled to the rotary-to-linear converter. Alternatively, a gear reduction may be interposed between the electric motor and the converter.

Figure 10:
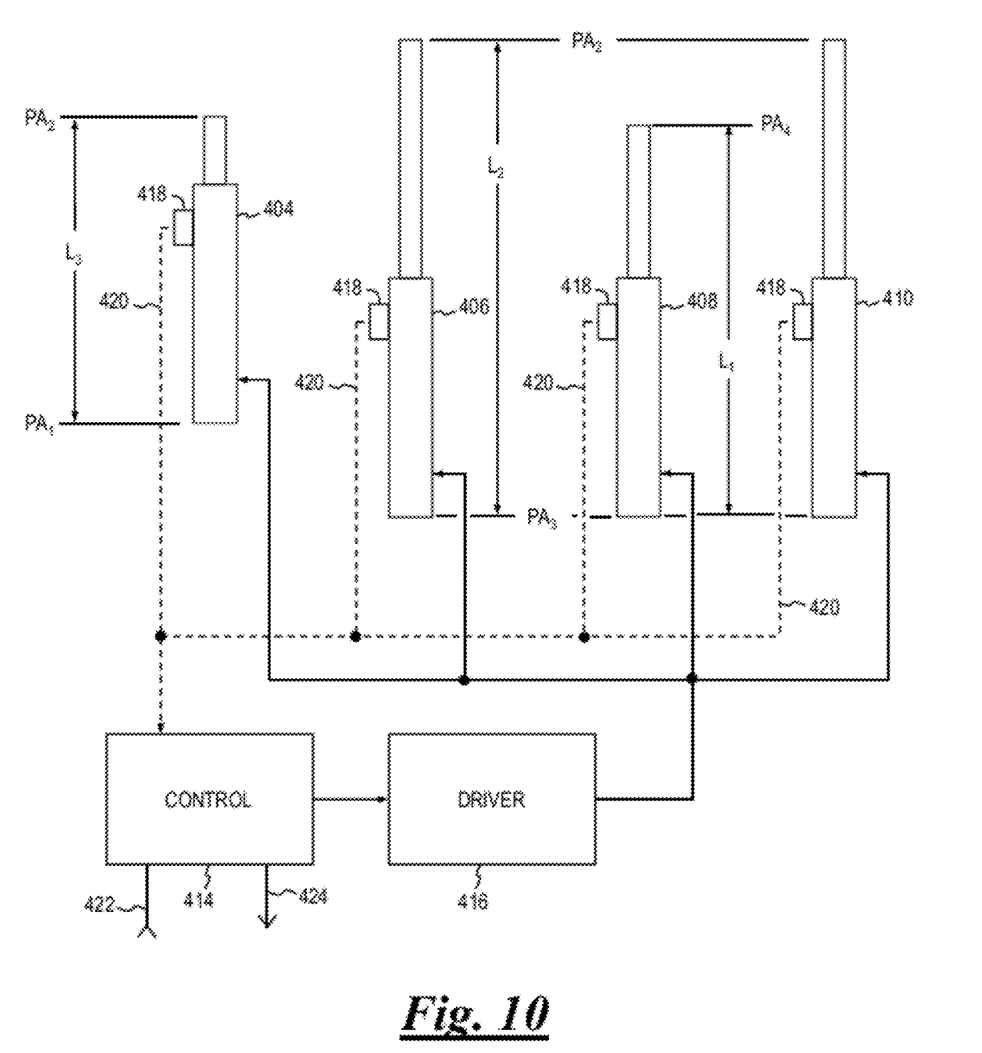
FIG. 10 is a block diagram of the general arrangement of a goniometer control system according to an embodiment of the present invention.
Figure 11:
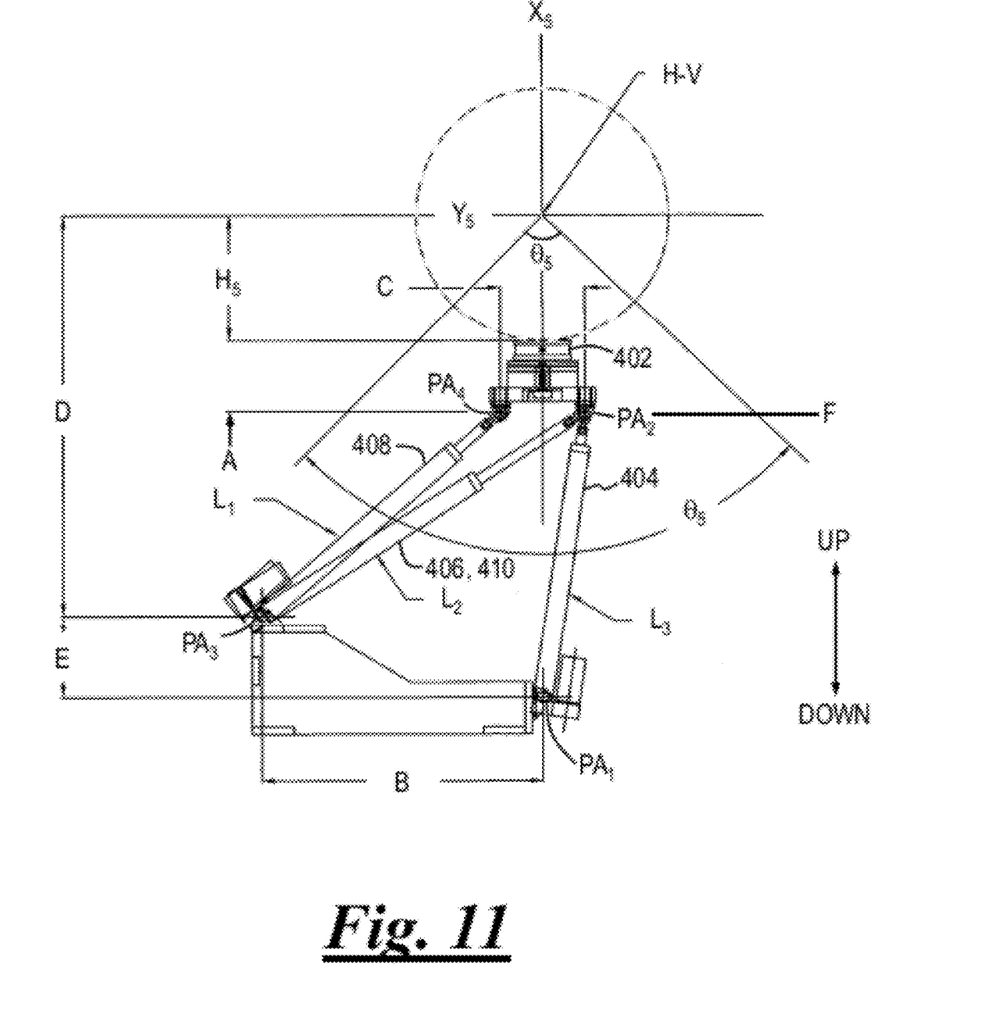
FIG. 11 shows the dimensional parameters associated with computations for positioning linear actuators of the goniometer system of FIG. 10.

FIGS. 10 and 11 show the general arrangement of a goniometer control system according to an embodiment of the present invention. A control 414 (which may be integral to system 400 or an external component coupled to the system) may include a microprocessor or other computing means and may operate in accordance with a set of predetermined instructions, such as a computer program, to resolve appropriate positions for platform 402 throughout a predetermined arc range of motion $\theta_5$. Once an appropriate platform 402 position is determined control 414 computes, using the programmed instructions, the appropriate extension positions $L_1$ for linear actuator 408, $L_2$ for linear actuators 406, 410 and $L_3$ for linear actuator 404 to achieve the desired position. Control 414 then operates linear actuators 404, 406, 408 and 410, via a driver 416, to provide electrical, hydraulic or other signals (represented by the solid arrows in FIG. 10) to move each actuator to their appropriate linear positions. The appropriate extension positions may be determined in an open-loop fashion, such by control 414 issuing a predetermined number of electrical output pulses via driver 416, the pulses being provided to a stepper motor 411 of each of linear actuators 404, 406, 408 and 410. Alternatively, the positions of linear actuators 404, 406, 408 and 410 may be controlled by control 414 in a closed-loop fashion using feedback elements 418 coupled to the linear actuators, the feedback elements each providing position feedback signals to control 414 for the linear actuator with which they are associated. Such feedback signals are generally represented by the broken line 420 in FIG. 10.

Figures 7, 8:
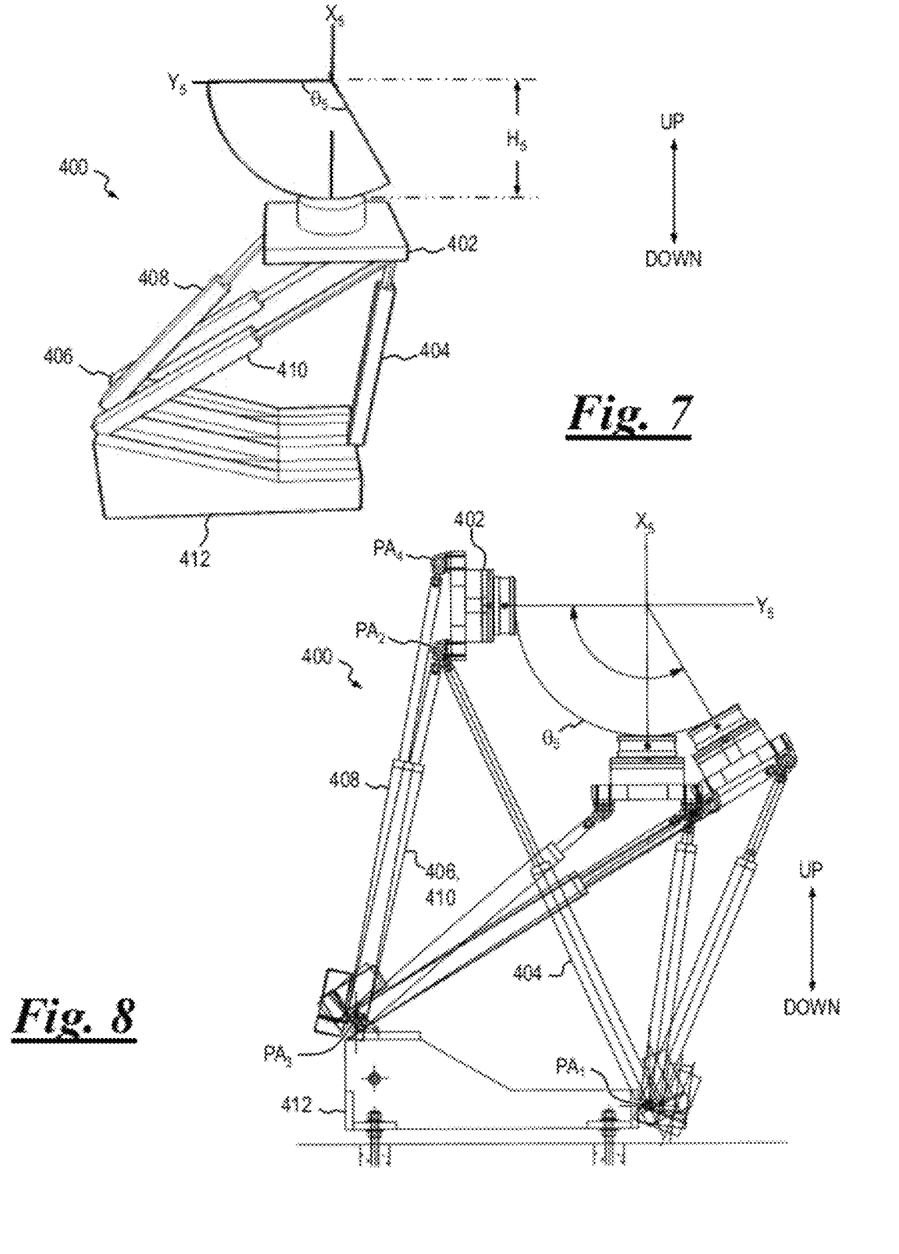
FIG. 7 is a side view of the goniometer system of FIG. 5.
FIG. 8 is an illustration of examples of multiple positions of a goniometer system according to an embodiment of the present invention.
Figures 9A, 9B, 9C, 9D:
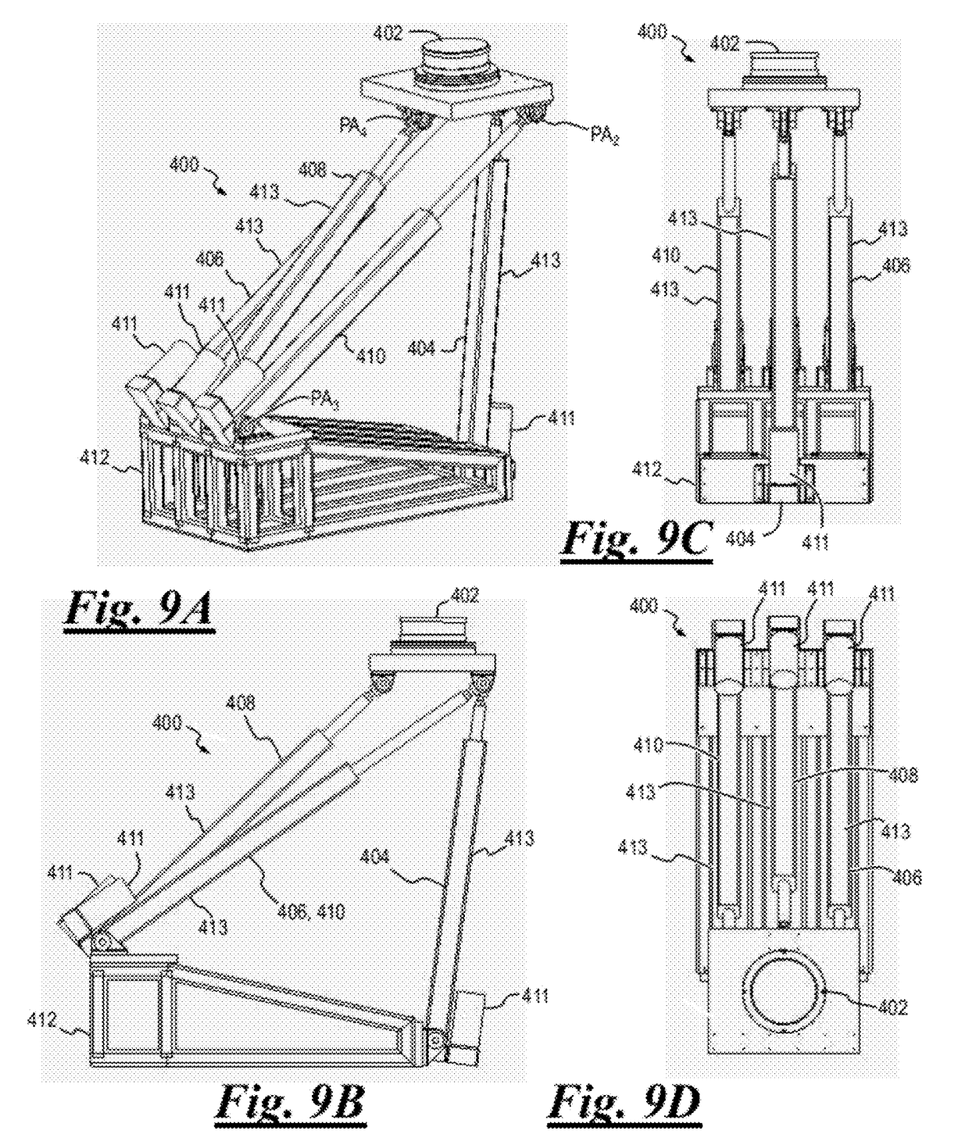
FIGS. 9A, 9B, 9C and 9D are perspective, side, end and top views respectively of the goniometer system of FIG. 8 according to an embodiment of the present invention.

With reference again to FIG. 8, in operation linear actuators 404, 406, 408 and 410 may be operated either individually, all together or in sub-groups to accurately and precisely position platform 402 to a number of predetermined positions and orientations about circular arc $\theta_5$, the linear actuators functioning together as a four-bar linkage. FIG. 8 shows platform 402 positioned at three discrete points of arc $\theta_5$, the platform being accurately and precisely positionable at any position about arc $\theta_5$ within the limits of travel of $L_1$ for linear actuator 408, $L_2$ for linear actuators 406, 410 and $L_3$ for linear actuator 404. Control 414 may be programmed to manually and/or automatically move platform 402 to the predetermined positions and orientations. Alternatively, control 414 may be configured to receive automatic and/or manual control signals from an external source (not shown), such as from an operator of the system or a computing device.

With reference to FIGS. 10 and 11, linear actuators 404, 406, 408 and 410 may each be extended or retracted to a determinable length to achieve a particular or select position of platform 402 about arc $\theta_5$ in accordance with Equations 1, 2 and 3, below. The L1, L2, and L3 lengths are a function of adjustable parameters, $\theta_5$ and H. The remaining parameters are fixed and are defined by the chosen geometry of system 400.

$$L_1 = \mathrm{SQRT}((B+(R*\mathrm{COS}(\theta_5+(A\ \mathrm{TAN}(-(C/2)/(H+A))))))^2+(D+(R*\mathrm{SIN}(\theta_5+(A\ \mathrm{TAN}(-(C/2)/(H+A))))))^2) \quad \text{Equation 1}$$

$$L_2 = \mathrm{SQRT}(B+(R*\mathrm{COS}(\theta_5+(A\ \mathrm{TAN}((C/2)/(H+A))))))^2+(D+(R*\mathrm{SIN}(\theta_5+(A\ \mathrm{TAN}((C/2)/(H+A))))))^2) \quad \text{Equation 2}$$

$$L_3 = \mathrm{SQRT}(((R*\mathrm{COS}(\theta_5+(A\ \mathrm{TAN}((C/2)/(H+A))))))^2+((D+E)+(R*\mathrm{SIN}(\theta_5+(A\ \mathrm{TAN}((C/2)/(H+A))))))^2) \quad \text{Equation 3}$$

where:

$L_1$ = length of actuator 408
$L_2$ = length of actuators 406, 410
$L_3$ = length of actuator 404
A = vertical distance between surface of platform 402 and a plane formed by pivot axes $PA_2$, $PA_4$
B = Horizontal distance between pivot axes $PA_1$, $PA_3$
C = Horizontal distance between pivot axes $PA_2$, $PA_4$
D = vertical distance from pivot axis $PA_3$ to H-V (theoretical center of rotation)
E = vertical distance from pivot axis $PA_1$ to pivot axis $PA_3$
R = SQRT $(H^2 + (C/2)^2)$
$\theta_5$ = select up-down tilt angle of platform 402
H = commanded height adjustment. For photometric testing H is generally specified so as to position the theoretical center of light for the item under test at the intersection of the $X_5$ and $Y_5$ axes (H-V).

These computations may be performed by control 414 and/or an external computer or similar device coupled to the control.

Control 414 may be implemented in any conventional form of analog or digital (e.g., a microprocessor or a computer) closed-loop servo controller having operational aspects including, but not limited to, force, velocity and directional controls for driver 416 and/or linear actuators 404, 406, 408 and 410. Control 414 may further include a predetermined set of logical instructions, such as a computer program, to define the various operational aspects of the control. Control 414 may also receive, via an input 422 (FIG. 10) instructions from an external device, such as photometric measurement equipment and/or calibration equipment.

The aforementioned position feedback elements provide information to control 414 relating to the positions of linear actuators 404, 406, 408 and 410. The feedback elements may be any conventional type of feedback element now known or later invented that is compatible with the architecture chosen for control 414, such as an absolute or relative position encoder. In other embodiments the feedback elements may be an arrangement of electromechanical or solid state limit switches or proximity-sensing elements located at predetermined positions. In some embodiments of linear actuators 404, 406, 408 and 410 utilizing a stepper or brushless DC motor a limit switch or proximity sensor at known or calibrated positions of linear actuators 404, 406, 408 and 410 may serve as index points for a predetermined set of instructions used by controller 414 to count the number of commutation pulses required to reach a predetermined position of the linear actuators. In addition to position information, the feedback elements may provide control 414 with information relating to the velocity of linear actuators 404, 406, 408 and 410 when they are moving.

In some embodiments of the present invention the aforementioned logical instructions (which may reside in control 414 and/or an external control, such as a computer terminal) may include a command to position platform 402 at a position which will be a function of "height" (which defines the radius of the arc of travel of the platform), an up/down angle about axis of rotation $Y_5$, and a right/left angle about axis of rotation $X_5$. The right/left angle of platform 402 may be directly set and/or measured in any conventional manner. The height and up/down angle position of platform 402 may be computed using an algorithm wherein the up/down angle, "ƒu/d," is a mathematical function of the extension lengths of actuators 404, 406, 408 and 410 (actuators 406 and 410 being generally the same length) at each commanded up/down position. In other words, the extension lengths of actuators 404, 406, 408 and 410 are a function of the commanded up/down angle and height.

Alternatively, system 400 may be commanded to move through arc $\theta_5$ (FIG. 8) at a prescribed speed while photometry equipment observing a test object (not shown) attached to platform 402 "scans on the fly" while measuring light emissions from the test object. In this embodiment the speed or "feed rate" of each linear actuator 404, 406, 408 and 410 is controlled in a predetermined manner. This motion requires the linear actuator 404, 406, 408 and 410 speeds to vary during the path of motion, and in some cases may require the direction of at least some of the linear actuators to reverse during the move. The movement of platform 402 may be controlled internally by control 414, or externally such as photometric measurement equipment and/or calibration equipment.

In one embodiment of the present invention it is desirable to maintain a "closed loop" form of position control of platform 402. In addition to the aforementioned position feedback elements 420 providing a positional communication back to control 414 regarding the status of linear actuators 404, 406, 408 and 410, a second set of encoders may be attached to each of the three length axes of the actuators to confirm in a precise manner whether the actuator is actually in the commanded position. If a difference in position greater than a predetermined tolerance is detected, then control 414 will act to readjust linear actuators 404, 406, 408 and 410 to achieve the commanded position. Control 414 may further include an output 424 providing data in any desired analog and/or digital format. The output data may include, without limitation, tilt and rotation angles for platform 402.

In some embodiments of the present invention platform 402 is rotatable to accommodate various lighting test requirements. Preferably, platform 402 is rotatable about axis of rotation $X_5$, which is oriented generally orthogonal to a plane "F" defined by pivot axes $PA_2$, $PA_4$ of the platform (FIG. 11).

Figure 12:
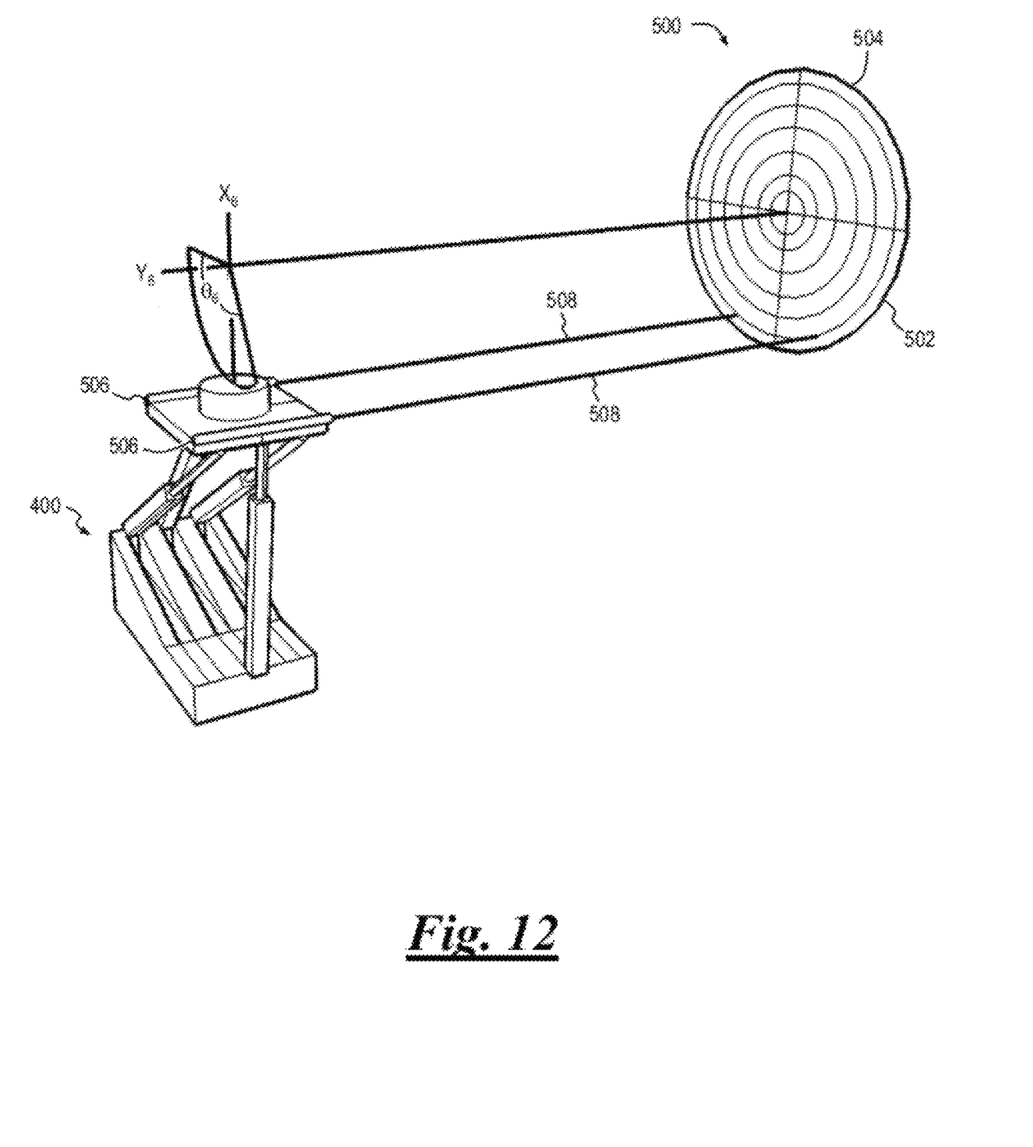
FIG. 12 shows a calibration system usable in conjunction with a goniometer system.

With reference to FIG. 12, in another embodiment of the present invention a target 500 consisting of a board 502 having concentric circles 504 of a contrasting color thereon may be used to calibrate system 400. Target 500 may be placed on a wall or on a stand perpendicular to the up/down tilt axis $Y_5$ of goniometer system 400 with its center at the "0,0" center of the rotational axis $X_5$ of the goniometer. A pair of laser emitters 506 may be mounted on the base of platform 402 so that, when energized, laser beams 508 emitted by the emitters travel about arc $\theta_5$ (FIG. 8) corresponding to the commanded positions of platform 402. This will provide a user with visual confirmation that system 400 is in the proper, commanded position. Alternatively, the proper up/down position of platform 402 may be verified using a bubble protractor. For precise confirmation of positions, one may also utilize a theodolite.

A comparison with prior art goniometer designs shows a number of advantages of the present invention. Firstly, the rotational interference between the edges of large items to be tested and the side frame members of the prior art box frame (FIGS. 1, 2) and half-frame (FIG. 3) configurations is completely eliminated. Thus, virtually any size object can be tested, so long as the object is within the load limitations of linear actuators 404, 406, 408 and 410 and so long as the object fits within the test room.

In many test facilities there is a limitation of the facility space available for installation of the goniometer positioner. Both the Type A (FIG. 1) and Type B (FIG. 2) prior art positioners require considerable space outside of the optical working area for the mechanism driving the motion of the device. This can force laboratory layouts that require excessive space. In some cases the size of the frame may be too large for the space intended. Often the size of the equipment causes extraordinary difficulties in shipping and in installation. Sometimes special doors may be required or it may even be necessary to remove a wall to move the system into the its final installed position. The present invention is compact, overcoming the drawbacks of prior art positioning systems.

System weight is also important, for several reasons. Firstly, shipping costs are always a concern and the weight and physical size of the goniometer will directly impact these costs. It is not unusual for the weight of a prior art goniometer system to exceed a thousand pounds. This limits the test facilities to those that can accommodate large, expensive goniometer installations. For example, an end user must be particularly concerned about the allowed load rating for the floor of the laboratory. This can be a significant issue for end users who desire to locate the goniometer in an upper-floor location where a thick concrete foundation is not usually available. In contrast, some configurations of the present invention are designed to weigh about 350 pounds, a substantial improvement over prior art systems.

Lastly, with regard to shipping, the present invention may be partly disassembled so that the components can be hand-carried to the testing site if necessary and then reassembled in place. Consequently, complex rigging equipment and large doors are not required to install the present invention.

While this invention has been shown and described with respect to a detailed embodiment thereof, it will be understood by those skilled in the art that changes in form and detail thereof may be made without departing from the scope of the claims of the invention.

What is claimed is:

1. A system for positioning an object, comprising:
a base;
a platform for detachably retaining the object;
a first linear actuator pivotably coupled to a first pivot axis of the platform and a first pivot axis of the base;
a second and a third linear actuator pivotably coupled to a second pivot axis of the base and the first pivot axis of the platform; and
a fourth linear actuator pivotably coupled to the second pivot axis of the base and a second pivot axis of the platform,
the first, second, third and fourth linear actuators being selectably adjustable in length to position the platform at a select position about a predetermined arc of travel.

2. The system of claim 1, further comprising a control coupled to the first, second, third and fourth linear actuators, the control selectably adjusting the lengths of the first, second, third and fourth linear actuators to position the platform at the select position.

3. The system of claim 2, further including a driver coupled between the control and the first, second, third and fourth linear actuators, the driver being configured to receive electrical control signals from the control and generate and supply drive signals to the first, second, third and fourth linear actuators to adjust their lengths.

4. The system of claim 2 wherein each of the first, second, third and fourth linear actuators each further include a feedback element arranged to generate an electrical signal corresponding to the length of the its associated linear actuator, the electrical signals being provided to the control.

5. The system of claim 2 wherein the control further includes one of a microprocessor and a computer.

6. The system of claim 5 wherein the control further includes a predetermined set of logical instructions executed by one of the microprocessor and the computer to define operational aspects of the control.

7. The system of claim 1 wherein the first, second, third and fourth linear actuators are electro-mechanical linear actuators.

8. The system of claim 7 wherein the first, second, third and fourth electro-mechanical linear actuators each include one of a dc brush motor, a dc brushless motor, a stepper motor and an induction motor.

9. The system of claim 7 wherein the first, second, third and fourth electro-mechanical linear actuators each include one of a lead screw and a ball screw.

10. The system of claim 1 wherein the platform is rotatable about a predetermined axis of rotation.

11. The system of claim 1, further including:
at least one laser emitter detachably coupled to the platform; and
a target spaced away from the platform,
the laser emitter and target cooperating to calibrate the system.

12. A system for positioning an object, comprising:
a base;
a platform for detachably retaining the object;
a first linear actuator pivotably coupled to a first pivot axis of the platform and a first pivot axis of the base;
a second and a third linear actuator pivotably coupled to a second pivot axis of the base and the first pivot axis of the platform;
a fourth linear actuator pivotably coupled to the second pivot axis of the base and a second pivot axis of the platform;
a control coupled to the first, second, third and fourth linear actuators; and
a feedback element coupled to each of the first, second, third and fourth linear actuators, each feedback element being arranged to generate an electrical feedback signal corresponding to the length of its associated linear actuator, the electrical feedback signals being provided to the control,
the control receiving the electrical feedback signals and selectably adjusting the lengths of the first, second, third and fourth linear actuators to position the platform at a select position about a predetermined arc of travel.

13. The system of claim 12, further including a driver coupled between the control and the first, second, third and fourth linear actuators, the driver being configured to receive electrical control signals from the control and generate and supply drive signals to the first, second, third and fourth linear actuators to adjust their lengths.

14. The system of claim 12 wherein the first, second, third and fourth linear actuators are electro-mechanical linear actuators.

15. The system of claim 14 wherein the first, second, third and fourth electro-mechanical linear actuators each include one of a dc brush motor, a dc brushless motor, a stepper motor and an induction motor.

16. The system of claim 14 wherein the first, second, third and fourth electro-mechanical linear actuators each include one of a lead screw and a ball screw.

17. The system of claim 12 wherein the control further includes one of a microprocessor and a computer.

18. The system of claim 12 wherein the control further includes a predetermined set of logical instructions executed by one of the microprocessor and the computer to define operational aspects of the control.

19. A method for positioning an object, comprising the steps of:
providing a base;
providing a platform for detachably retaining the object;

pivotably coupling a first adjustable-length member between a first pivot axis of the platform and a first pivot axis of the base;

pivotably coupling a second and a third adjustable-length member between a second pivot axis of the base and the first pivot axis of the platform; and pivotably coupling a fourth adjustable-length member between the second pivot axis of the base and a second pivot axis of the platform, and selectably adjusting the lengths of the first, second, third and fourth linear actuators to position the platform at a select position about a predetermined arc of travel.

20. The method of claim 19, further comprising the step of configuring the platform to rotate about a predetermined axis of rotation.

\* \* \* \* \*